(12) United States Patent
Clough et al.

(10) Patent No.: US 8,779,179 B2
(45) Date of Patent: Jul. 15, 2014

(54) SYNTHESIS OF SILYL ACETYLENES

(75) Inventors: Robert S. Clough, St. Paul, MN (US); John E. Anthony, Lexington, KY (US); Marcia M. Payne, Lexington, KY (US)

(73) Assignee: 3M Innovative Properties Company, St. Paul, MN (US)

( * ) Notice: Subject to any disclaimer, the term of this patent is extended or adjusted under 35 U.S.C. 154(b) by 41 days.

(21) Appl. No.: 13/639,876

(22) PCT Filed: May 18, 2011

(86) PCT No.: PCT/US2011/036960
§ 371 (c)(1),
(2), (4) Date: Oct. 8, 2012

(87) PCT Pub. No.: WO2011/149735
PCT Pub. Date: Dec. 1, 2011

(65) Prior Publication Data
US 2013/0150606 A1    Jun. 13, 2013

Related U.S. Application Data

(60) Provisional application No. 61/349,380, filed on May 28, 2010.

(51) Int. Cl.
*C07F 7/02* (2006.01)
*C07F 7/08* (2006.01)

(52) U.S. Cl.
CPC .............. *C07F 7/0805* (2013.01); *C07F 7/0827* (2013.01)
USPC ........... 556/476; 556/477; 556/478; 556/480; 556/481

(58) Field of Classification Search
CPC .......... C07F 7/123; C07F 7/16; C07F 7/0883; C07F 7/0896; C07F 7/12; C07F 7/122; C07F 7/126; C07F 7/08; C07F 7/083; C07F 7/0861; C07F 7/1888
USPC .......................... 556/476, 477, 480, 481, 478
See application file for complete search history.

(56) References Cited

U.S. PATENT DOCUMENTS

| | | | |
|---|---|---|---|
| 5,068,368 | A | 11/1991 | Smith |
| 5,196,138 | A | 3/1993 | Smith |
| 5,342,984 | A | 8/1994 | Kubota |
| 6,690,029 | B1 | 2/2004 | Anthony |
| 7,576,208 | B2 | 8/2009 | Brown |
| 2006/0220007 | A1 | 10/2006 | Bailey |
| 2007/0137520 | A1 | 6/2007 | Brown |
| 2008/0191199 | A1 | 8/2008 | Anemian |
| 2008/0197325 | A1 | 8/2008 | Leeming |

FOREIGN PATENT DOCUMENTS

| | | |
|---|---|---|
| JP | 7252271 | 10/1995 |
| WO | WO 2005-055248 | 6/2005 |
| WO | WO 2006-119853 | 11/2006 |
| WO | WO 2008-128618 | 10/2008 |
| WO | WO 2009-079150 | 6/2009 |
| WO | WO 2009-155106 | 12/2009 |
| WO | WO 2010-138807 | 12/2010 |
| WO | WO 2011-150020 | 1/2011 |

OTHER PUBLICATIONS

Iwata; Journal of Organometallic Chemistry, 667, 2003, 90-95).*
Corriu, "(Ethynylhydrosilane) cobalt Carbonyl Complexes. Reactivity of the Silicon-Hydrogen Bond", *Organometallics*, vol. 9, 1990, pp. 2086-2091.
Haddon, "Band Electronic Structure of One- and Two-Dimensional Pentacene Molecular Crystals", *J. Phys. Chem. B*, 2002, vol. 106, pp. 8288-8292.
Hoffmann, "Selective Synthesis of Functional Alkynylmono- and -trisilanes", *Eur. J. Inorg. Chem*, vol. 7, 2010, pp. 1133-1142.
Iwata, $PdCl_2$ and $NiCl_2$-catalyzed hydrogen-halogen exchange for the convenient preparation of bromo- and iodosilanes and germanes, *Journal of Organometallic Chemistry*, vol. 667, 2003, pp. 90-95.
Midland, "Preparation and Use of Lithium Acetylide: 1-Methyl-2-Ethynyl-endo-3,3-Dimthy1-2-Norbornanol", *Organic Syntheses*, 1990, Coll., vol. 68, p. 14; and 1993, Coll. vol. 8, p. 391 (1993).
Tanino, "Synthesis of cyclic allenylsilanes via an intramolecular substitution reaction of 1-siloxy-2, 3-epoxyalkanes", *Tetrahedron Letter*, Elsevier, Amsterdam, NL, 2000, vol. 41, No. 48, pp. 9281-9285.
Troisi, "Electronic Interactions and Thermal Disorder in Molecular Crystals Containing Cofacial Pentacene Units", *Chem. Mater.*, 2005, vol. 17, pp. 5024-5031.
Wander, "Synthesis of Polyaryl Rigid-Core Carbosilane Dendrimers for Supported Organic Synthesis", *Organometallics*, 2009, vol. 28, pp. 4406-4415.
Wrackmeyer, "1-Silacyclopent-2-enes and 1-silacyclohex-2-enes bearing functionally substituted silyl groups in 2-positions. Novel electron-deficient Si-H-B bridges", *Applied Organometallic Chemistry*, 2006, vol. 20, pp. 99-105. [Published online Nov. 21, 2005 in Wiley InterScience (www.interscience.wiley.com). DOI:10.1002/aoc.1020.
International Search Report for PCT/US2011/036960, Mailed Jul. 18, 2011, 3 pages.

* cited by examiner

*Primary Examiner* — Sudhakar Katakam
*Assistant Examiner* — Pancham Bakshi
(74) *Attorney, Agent, or Firm* — Kent S. Kokko

(57) ABSTRACT

The present disclosure provides a method of preparing silylethynyl compounds in which two of the hydrocarbyl groups bonded to the silicon exclusive of the ethynyl group, are the same and one is different, that may be used in preparing novel silylethynyl functionalized acene semiconductor chromophores.

11 Claims, No Drawings

SYNTHESIS OF SILYL ACETYLENES

CROSS REFERENCE TO RELATED APPLICATION

This application claims the benefit of U.S. Provisional Patent Application No. 61/349,380, filed May 28, 2010, the disclosure of which is incorporated by reference herein in its entirety.

BACKGROUND

Acenes, as a class of graphite substructures, are particularly attractive targets in the synthesis of organic semiconductors because of their demonstrated high mobilities, strong intermolecular coupling and small reorganization energies. The usefulness of acene oligomers such as pentacenes are already showing in numerous electronics applications including, but not limited to, thin-film transistors (display technologies), photovoltaic cells and light-emitting diodes.

Substituted acenes have received limited attention due to their synthetic inaccessibility. More specifically, while the properties and limitations of simple, linear conjugated organic systems have been well studied by either synthesis or structure-property determinations performed on series of oligomers, few such studies have been performed on fused aromatic systems, simply because of a lack of synthetic methodology available for their preparation. Although a number of researchers have made excellent approaches to planarized graphitic oligomers and polymers, and simple fused aromatic systems based on the graphite lattice are already being explored for the construction of field effect transistors (FETs) and molecular electronic devices, the lack of a reliable route to synthetically-tailored linearly fused aromatics has precluded the development of fully tunable organic materials.

The ability to tailor organic materials to maximize film-forming abilities or solid-state order cannot be understated, as such customization will allow the use of such systems as components for RFID tags, flexible displays, light-weight solar panels and ubiquitous semiconductor electronics. Functionalization is critical to enable exploration of self-organization in these graphite-like systems. Pendant groups on an oligoacene can be used to alter the solubility, stability and solid-state ordering of the material. Numerous studies of organic semiconductors, including band structure and exchange integral calculations, have shown that subtle changes in semiconductor crystal packing in systems such as the silylethyne-substituted acenes can yield dramatic increases in mobility. See J. E. Anthony et al., *J. Phys. Chem. B*, 2002, 106, 8288; and J. E. Anthony, et al, *Chem. Mater.* 2005, 17, 5024.

A number of attempts at modification of packing in current high-performance semiconductors have indeed shown such improvements; for example, alkylation of pentacene, or halogenation of anthradithiophene chromophores led to changes in crystallization or crystal packing that improved performance relative to the parent hydrocarbon. Unfortunately, these approaches require significant additional synthesis steps, and reduce the low-cost advantage promised by organic semiconductors.

SUMMARY

The present disclosure provides a method of preparing silylethynyl compounds in which two of the hydrocarbyl groups bonded to the silicon exclusive of the ethynyl group, are the same and one is different, that may be used in preparing novel silylethynyl functionalized acene semiconductor chromophores. The silylethyne approach to functionalizing semiconductor chromophores allows straightforward engineering of solid-state order by the simple alteration of the trialkylsilyl substituent. Changes in the groups on the silane yield a variety of pi-stacked structures, and for compounds of similar pi-stacked structure, such as one-dimensional pi-stacked materials, changes to the trialkylsilyl groups have yielded dramatically different thermal properties. Further investigation of the effect of the trialkylsilyl groups on the properties and electronic performance of the silylethynyl functionalized acenes have been hampered by the absence of versatile, efficient synthetic approaches to unsymmetrical silyl acetylenes, i.e. silyl acetylenes in which the three substituents on the silicon other than the ethynyl or acetylene group are not identical.

The present disclosure provides an improved method of preparing silyl acetylenes (also referred to as ethynylsilanes), in which two of the hydrocarbyl groups bonded to the silicon are the same and one is different, that may be used in preparing novel silylethynyl functionalized acenes using the methods described in WO 2009/155106 (Anthony et al.). The method provides silyl acetylenes of higher purity in a more economical manner. Purity of the silyl acetylene is important as it impacts the purity of the silylethynyl functionalized acene, and thus can dictate the purification process required to afford high purity acenes for use in electronic devices. Small levels of impurities in the silylethynyl functionalized acene semiconductors can be detrimental to electronic performance characteristics such as charge carrier mobility, ON/OFF current ratio, and OFF current, and can effect device stability.

The silylethynyl compounds that may be prepared by the method of this disclosure are of the formula

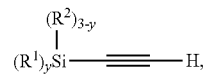

where $R^1$ and $R^2$ are (hetero)hydrocarbyl groups, and $R^1$ is not $R^2$, and y is 1 or 2.

The present disclosure provides an improved method of preparing silyl acetylenes (also referred to as silylethynyl compounds), in which two of the hydrocarbyl groups bonded to the silicon are the same and one is different, that may be used in preparing novel silylethynyl functionalized acenes. The method provides silyl acetylenes of higher purity in a more economical manner. Purity of the silyl acetylene is important as it impacts the purity of the silylethynyl functionalized acene, and thus can dictate the purification process required to afford high purity acenes for use in electronic devices. Small levels of impurities in the silylethynyl functionalized acene semiconductors can be detrimental to electronic performance characteristics such as charge carrier mobility, ON/OFF current ratio, and OFF current, and can effect device stability.

The ability to tailor organic materials to maximize film-forming abilities or solid-state order cannot be understated, as such customization will allow the use of such materials in low-cost or large-area electronics (e.g. RFID tags), as the backplane in flexible flat-panel displays or as donors or acceptors in solar panels. Functionalization will also allow the exploration of self-organization in these graphite-like systems. Pendant groups on an oligoacene can be used to alter the solubility, stability and solid-state ordering of the material.

The instant method provides silylethynyl compounds that enable the further preparation of functionalized acene compounds which, in turn, influence the processability, solid-state order and stability of the resulting material, and in many embodiments, improved electronic properties.

As used herein:

"Alkyl" refers to a monovalent group that is a radical of an alkane, which is a saturated hydrocarbon. The alkyl can be linear, branched, cyclic, or combinations thereof and typically contains 1 to 30 carbon atoms. In some embodiments, the alkyl group contains 1 to 30, 4 to 30, 1 to 20, 4 to 20, 1 to 14, 1 to 10, 4 to 10, 4 to 8, 1 to 8, 1 to 6, or 1 to 4 carbon atoms. Examples of alkyl groups include, but are not limited to, methyl, ethyl, n-propyl, iso-propyl, cyclopropyl, n-butyl, tert-butyl, iso-butyl, n-pentyl, n-hexyl, cyclohexyl, n-octyl, n-heptyl, and ethylhexyl.

"Alkenyl" refers to a monovalent group that is a radical of an alkene, which is a hydrocarbon with at least one carbon-carbon double bond. The alkenyl can be linear, branched, cyclic, or combinations thereof and typically contains 2 to 30 carbon atoms. In some embodiments, the alkenyl contains 2 to 20, 2 to 14, 2 to 10, 4 to 10, 4 to 8, 2 to 8, 2 to 6, or 2 to 4 carbon atoms. Exemplary alkenyl groups include ethenyl, propenyl, isopropenyl, allyl, and 2-but-1-enyl.

"Alkynyl" refers to a monovalent group that is a radical of an alkyne, a hydrocarbon with at least one carbon-carbon triple bond. The alkynyl can be linear, branched, cyclic, or combinations thereof and typically contains 2 to 30 carbon atoms. In some embodiments, the alkynyl contains 2 to 20, 2 to 14, 2 to 10, 4 to 10, 4 to 8, 2 to 8, 2 to 6, or 2 to 4 carbon atoms. Exemplary alkynyl groups include ethynyl, propynyl, and butynyl. Some alkynyl groups such as an ethynyl can be further substituted with a silyl group.

"Aryl" refers to a monovalent group that is a radical of an aromatic carbocyclic compound. The aryl can have one aromatic ring or can include up to 5 carbocyclic ring structures that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

"Aralkyl" refers to an alkyl substituted with an aryl group.

"Halo" refers to a halogen group (i.e., —F, —Cl, —Br, or —I).

"Haloalkyl" refers to an alkyl that is substituted with one or more halo groups.

"heteroalkyl" includes both straight-chained, branched, and cyclic alkyl groups with one or more heteroatoms independently selected from S, O, and N with both unsubstituted and substituted alkyl groups. Unless otherwise indicated, the heteroalkyl groups typically contain from 1 to 20 carbon atoms. "Heteroalkyl" is a subset of "hydrocarbyl containing one or more S, N, O, P, or Si atoms" described below. Examples of "heteroalkyl" as used herein include, but are not limited to, methoxy, ethoxy, propoxy, 3,6-dioxaheptyl, 3-(trimethylsilyl)-propyl, 4-dimethylaminobutyl, and the like. Unless otherwise noted, heteroalkyl groups may be mono- or polyvalent.

"(hetero)alkyl" includes both alkyl and heteroalkyl.

"heteroaryl" is aryl containing 1-3 heteroatoms such as nitrogen, oxygen, or sulfur and can contain fused rings. Some examples of heteroaryl groups are pyridinyl, furanyl, pyrrolyl, thienyl, thiazolyl, oxazolyl, imidazolyl, indolyl, benzofuranyl, and benzthiazolyl.

"(hetero)aryl" includes both "heteroaryl" and aryl.

"hydrocarbyl" refers to groups containing only hydrogen and carbon, including cyclic or acyclic alkyl, alkenyl, alkynyl, and aryl groups.

As used herein, "(hetero)hydrocarbyl" is inclusive of hydrocarbyl alkyl and aryl groups, and heterohydrocarbyl heteroalkyl and heteroaryl groups, the later comprising one or more catenary oxygen heteroatoms such as ether or amino groups. Heterohydrocarbyl may optionally contain one or more catenary (in-chain) functional groups including ester, amide, urea, sulfonamide urethane, and carbonate functional groups. Unless otherwise indicated, the non-polymeric (hetero)hydrocarbyl groups typically contain from 1 to 60 carbon atoms.

"Silylethynyl" refers to a monovalent group of formula —C≡C—Si($R^a$)$_3$ where $R^a$ is independently selected from hydrogen, alkyl, alkoxy, alkenyl, heteroalkyl, hydroxyalkyl, aryl, aralkyl, heteroaryl, or heteroaralkyl. These groups are sometimes referred to as silanylethynyl groups.

DETAILED DESCRIPTION

In the method of this disclosure, a halohydrocarbylsilane of formula I is provided

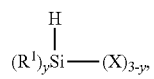

wherein
X is a leaving group such as halogen or triflate, preferably Cl or Br, y is 1 or 2, and $R^1$ is a (hetero)hydrocarbyl group, preferably a hydrocarbyl group and more preferably a alkyl group, including cycloalkyl, or an alkenyl group. Such compounds are readily prepared e.g. by the hydrosilylation of alkenes by dichlorosilane, and many are commercially available, including diisopropylchlorosilane and allyl dichlorosilane Compounds of Formula I are reacted, in a suitable solvent, with an organometallic reagent of the formula:

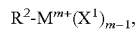

wherein $M^{m+}$ an alkali- or alkali earth metal cation of valence m, where m is 1 or 2, $X^1$ is a halide, $R^2$ is a (hetero)hydrocarbyl group, and y is 1 or 2.

Preferably $R^2$ is selected to be different from $R^1$ as trihydrocarbylsilyl halides with three identical hydrocarbyl groups are more available and may be prepared by a variety of different methods. Preferably $R^2$ is selected from an alkyl, aryl or alkenyl group. To the availability and/or ease of preparation, preferably the organometallic reagent is a Grignard reagent, or a organolithium reagent.

Representative examples of organometallic reagents that are suitable for use in the process of this invention are methylmagnesium halide, ethylmagnesium halide, n-propylmagnesium halide, isopropenylmagnesium halide, n-butylmagnesium halide, butenylmagnesium halide, n-hexylmagnesium halide, tetramethylenedimagnesium dihalide, n-octylmagnesium halide, phenylmagnesium halide, adamantylmagnesium halide, 1-tetradecylmagnesium halide, 3-methylbenzylmagnesium halide, crotylmagnesium halide, 4-hexadecylphenylmagnesium halide, vinylmagnesium halide, allylmagnesium halide and cyclpropylmagnesium halide. Preferably the halide is bromide, chloride or iodide. Further, propyllithium, cyclopropyllithium, vinyllithium, propenyllithium, allyllithium, isopropenyllithium, and butenyllithium are examples of organolithium reagents that might be selected for addition to the halosilane. As would be understood by one skilled in the art, other corresponding alkali metal compounds could also be used.

Stoichiometric amounts of the organometallic reagent are preferably used in this reaction. However, an excess of up to 200 mole percent of the organometallic reagent, with a preferred excess of up to 100 mole percent, and a more preferred excess of 5 to 25 mole percent, can be employed, relative to the molar equivalents of the halogen X.

Suitable solvents include tetrahydrofuran, hexanes, heptane, 1,2-dimethoxyethane, and ether, or mixtures of these solvents, for example. The aforesaid reaction is typically run for a period of time from 0.5 hours to 48 hours, generally 1 hour, at a temperature from −78 to 40° C., generally from −78 to 0° C. The aforesaid reaction is typically run for a period of time from minutes to several hours to 48 hours, generally 1 hour.

The product of the above reaction is of the formula:

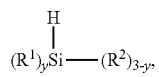

II where
$R^1$ and $R^2$ are (hetero)hydrocarbyl groups, and $R^1$ is not $R^2$, and y is 1 or 2.

Compounds of Formula II are then subjected to a hydrogen-bromine exchange reaction using a group 10 transition metal catalyst in the presence of an alkyl or alkenyl bromide compound to convert the hydrosilane to a bromosilane. Such transition metal mediated exchange reactions were found to provide high yields of the desired bromosilane or silyl bromide, minimal byproducts, and the catalyst residue was easily separated from the product. Other methods for effecting this conversion, such as the use of the brominating agents N-bromosuccinimide or bromine afforded more byproducts and often decreased yields The Group 10 catalyst used in this reaction may be metal palladium, platinum or nickel. The catalyst may be, in addition to the zero valent metal, salts such as chlorides, acetates, propionate and bisacetylacetonatopalladium; and metal complexes such as benzonitrile complexes, acetonitrile complexes, and triphenylphosphine complexes. In principle, this reaction does not require the use of any reaction solvent, but aprotic reaction solvents such as tetrahydrofuran, benzene toluene and decalin may be used in the reaction If zero valent metal catalyst is used, it is preferably used in the form of powder because of its high surface area and, in particular, the metal catalyst is used in the form of an active carbon- or alumina-supported catalyst since it can easily be handled.

The hydrogen-bromine transition metal catalyst mediated exchange takes place in the presence of an aliphatic bromide, including alkyl and alkenyl bromides. Specific example of aliphatic bromides include methyl bromide, ethyl bromide, n- and iso-propyl bromide, n-, sec- and isobutyl bromide, allyl bromide, methallyl bromide, 3-bromo-1-butene, and 1-bromo-3-pentene.

The amount of the aliphatic bromide reacted with the trihydrocarbylsilane of Formula II ranges from 1 to 2 times the equivalent amount of the latter. The amount of the catalyst used in the reaction ranges from 1 to 10000 ppm and preferably 10 to 1000 ppm on the basis of the amount of the trihydrocarbylsilane.

The reaction is carried out at a temperature preferably ranging from 40 to 150° C. and is generally conducted under an inert atmosphere.

Specifically, the foregoing reaction permits the preparation of compounds of the formula III:

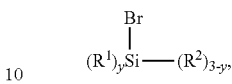

where $R^1$ and $R^2$ are (hetero)hydrocarbyl groups, and $R^1$ is not $R^2$, and y is 1 or 2.

The bromo compound of Formula III may be ethynylated to the desired silylethynyl compound by nucleophilic displacement of the bromine by an acetylide. More specifically, the compound of Formula III may be reacted with an alkali- or alkali earth metal acetylide of the formula

where M+ is an alkali- or alkali earth metal cation, $R^3$ is H— or an acetylene protecting group such as $(CH_3)_3$—Si—. In some embodiments, the corresponding Grignard reagent may be used.

The term "protecting group" refers to any group which when bound to one or more ethynyl groups of the compounds described herein will prevent reactions from occurring at these protected functionalities and which protecting group can be removed by conventional chemical steps to reestablish the unprotected ethynyl functional group. The particular removable blocking group employed is significant, as it must be selectively removed in the presence of the desired silyl group. Suitable protecting groups for various functional groups as well as suitable conditions for protecting and deprotecting particular functional groups are well known in the art. For example, numerous protecting groups are described in W. Greene and Wuts, Protecting Groups in Organic Synthesis, Third Edition, Wiley, New York, 1999, and references cited therein.

Preferably the ethynyl protecting groups is selected from lower trialkylsilanes such as trimethylsilyl, (3-cyanopropyl) dimethylsilyl. triethylsilyl. t-butyldimethylsilyl, hexyldimethylsilyl, benzyldimethylsilyl, dimethyl[1,1-dimethyl-3-(tetrahydro-2H-pyran-2-yloxy)propylsilyl, biphenyldimethylsilyl, methylol, —CHO, and —CH$(OCH_3)_2$. Such protecting groups may be subsequently removed by methods known in the art including treatments with dilute base or fluoride ion.

The acetylide may be prepared by techniques know in the art. For example, it may be prepared by reacting the acetylene compound with a lithium alkyl or lithium amide reagent. Such methods are described, for example in Organic Syntheses, Coll. Vol. 8, p. 391 (1993); Vol. 68, p. 14 (1990), and U.S. Pat. No. 5,068,368 or 5,196,138 (Smith et al.). The acetylide so generated is then contacted with the bromo compound of Formula III.

In embodiments where $R^3$=H, the acetylide may be prepared in situ by bubbling acetylene gas though a solution or suspension of an alkyl lithium or lithium amide compound in an inert solvent. Alternatively, ethynylmagnesium bromide (ethynyl Grignard) can be purchased as a commercial solution from a number of vendors (including Sigma-Aldrich).

In embodiments where $R^3$ is $(CH_3)_3$—Si—, the product may be desilylated by contacting with a suitable desilylating agent. Such desilylating reagents include catalytic amounts (5% to 10%, mol:mol) of fluoride compounds such tetrabutylammonium fluoride or other desilylating reagents described in Greene and Wuts, "Protecting Groups in Organic Synthesis," (John Wiley & Son Press, 2nd Ed) may be employed. Suitable solvents include ether, tetrahydrofuran, dichloromethane, ethanol, methanol and toluene, for example. The aforesaid reaction is run for a period of time from 0.5 hours to 5 hours, generally 1 hour, at a temperature from 0 to 40° C., generally from 10 to 25° C. In some embodiments, dilute base may be used (such as sodium hydroxide, potassium carbonate, potassium cabonate) in an alcoholic solvent, or an alcoholic solvent with a solubilizing co-solvent such as tetrahydrofuran or diethyl ether.

EXAMPLES

All parts, percentages, ratios, etc. in the examples are by weight, unless noted otherwise. Solvents and other reagents used were obtained from Sigma-Aldrich Chemical Company, Milwaukee, Wis. unless specified differently.
Materials Ammonium chloride (crystal) and magnesium sulfate (anhydrous $MgSO_4$) were obtained from Mallinckrodt Baker, Inc., Phillipsburg, N.J.

Anhydrous tetrahydrofuran (anhydrous THF), which had >99.9% purity and was inhibitor-free, was obtained from Sigma-Aldrich Chemical Company, Milwaukee, Wis.

Reagent tetrahydrofuran (THF), an A.C.S. reagent which had >99.9% purity, was obtained from Sigma-Aldrich Chemical Company, Milwaukee, Wis.

Benzene was obtained from Sigma-Aldrich Chemical Company, Milwaukee, Wis. and dried by boiling off 10% volume prior to use.

n-Butyllithium (2.5 M in hexanes), allyl bromide, isopropenylmagnesium bromide (0.5 M in THF), allylmagnesium chloride (2.0 M in THF), sulfuric acid (A.C.S. reagent, 95-98%) were obtained from Sigma-Aldrich Chemical Company, Milwaukee, Wis.

Diisopropylchlorosilane was obtained from Gelest Chemicals, Morrisville, Pa.

Pentane, dichloromethane, and hexanes were obtained from Pharmco-Aaper, Shelbyville, Ky.

Quantitative filter paper was obtained from VWR, West Chester, Pa.
Test Methods

Gas Chromatography-Mass Spectroscopy (GC-MS) Analysis Method 1

Samples were dissolved in pentane at 1 mg/mL prior to analysis. GC-MS analysis was carried out using an Agilent 6890 Network GC system and Agilent 5973 Network Mass Selective Detector. The initial oven column temperature was 70° C., with a two minute hold at that temperature, then the temperature was ramped up at a rate of 20° C./min. The pressure was $4.2 \times 10-5$ torr.

Gas Chromatography-Mass Spectroscopy (GC-MS) Analysis Method 2

Samples were dissolved in dichloromethane at 10 mg/mL prior to analysis and the solutions were placed into sealed autosampler vials.

Method for EI (Electron Ionization)/GC/MS:

EI/GC/MS was carried out using an Agilent model 5973 GC/MSD equipped with a model 6890 GC and a model 7673 liquid autosampler.

1 μL of solution was injected into the GC with a 40:1 split. The injector temperature was held at 250° C. while the transfer line to the MS detector was held at 300° C. The separation was performed on a Phenomenex Zebron ZB-5 ms capillary column with 30 m length, 250 μm ID, and 25 μm film thickness. Helium carrier gas was used with a flow rate of 1.5 mL/min. The initial column oven temperature was 40° C. and was ramped to 310° C. at a rate of 10° C./min. The final temperature was held for 8 minutes for a total run time of 35 minutes. The column eluent was analyzed by electron ionization (EI) mass spectrometry with no solvent delay using an electron energy of 70 eV with a source temperature of 230° C. The mass spectra were obtained using a quadrupole mass filter which was scanned from 29-550 m/z.

Method for CI (Chemical Ionization)/GC/MS:

CI/GC/MS was carried out using a Thermo ITQ 1100 ion trap GC/MS equipped with a TRACE GC Ultra and a TriPlus liquid autosampler.

1 μL of solution was injected into the GC with a 20:1 split. The injector temperature was held at 250° C. while the transfer line to the MS detector was held at 250° C. The separation was carried out using a J&W DB-5 ms capillary column with a 30 m length, 250 μm ID, and 25 μm film thickness. Helium carrier gas was used with a flow rate of 1.5 mL/min. The initial column temperature was 40° C. and was ramped to 320° C. at 20° C./min. and held at the final temperature for 5 minutes. This resulted in a shorter runtime of 19 minutes which was beneficial in increasing throughput as several different CI reagent gases and conditions were used to determine or verify the molecular weight of the compounds in the sample mixtures. The column eluent was analyzed by chemical ionization (CI) with methane and ammonia reagent gases introduced at flow rates of 1, 1.5, 2, and 3 mL/min. Ionization of the reagent gas and eluent began after a 2 minute delay for the dichloromethane solvent. The ionized analytes were transferred to the ion trap analyzer which was scanned from 60-800 m/z.

1H-NMR Spectroscopy $^1$H NMR spectroscopy was performed with a Varian Unity 400 MHz spectrometer.

Preparative Examples

Preparation of Allyldiisopropylsilane

Diisopropylchlorosilane (2.11 g, 14.0 mmol) was dissolved in anhydrous THF (12 mL) and treated with 1.2 equivalents of allylmagnesium chloride (8.4 mL, 2.0 M in THF, 16.8 mmol). The reaction was heated to 40° C. for 4 hours, then cooled and quenched with water (10 mL) and dilute sulfuric acid (10 mL), and extracted into pentane (2×50 mL). The organic layers were combined and washed with water (5×10 mL), then dried over $MgSO_4$, filtered, and concentrated via rotary evaporator (carefully, product is volatile) to yield crude allyldiisopropylsilane (1.9 g). No further purification was performed.

Preparation of Isopropenyldiisopropylsilane—Method 1

0.5 M isopropenylmagnesium bromide in THF (Aldrich, 365 mL, 182 mmol, 1.1 eq. to silane) was added dropwise at 0° C. to diisopropylchlorosilane (25 g, 166 mmol) in anhydrous THF (50 mL). The reaction mixture was heated to 40° C. overnight (15 hours), then cooled and quenched with water (50 mL) and dilute sulfuric acid (50 mL). Pentane (150 mL) was added and the organic layer was separated, washed repeatedly with water (8×50 mL), dried over $MgSO_4$, and filtered. The solution was concentrated (carefully, product is volatile) on a rotary evaporator to yield 22.9 g of crude product as a light brown liquid. No further purification was performed.

Preparation of
Isopropenyldiisopropylsilane—Method 2

0.5 M isopropenylmagnesium bromide in THF (Aldrich, 320 mL, 160 mmol, 1.1 eq. to silane) was added dropwise at 0° C. to diisopropylchlorosilane (22 g, 145 mmol) in anhydrous THF (40 mL). The reaction mixture was heated to 40° C. for 8 hours, then cooled and quenched with water (50 mL) and dilute sulfuric acid (50 mL). The crude product was extracted into pentane, washed with water and brine, dried over $MgSO_4$, filtered and concentrated. Careful removal of solvent (product is volatile) yielded 22 g of crude isopropenyldiisopropylsilane as a pale yellow liquid that was not subjected to further purification.

Example 1

Synthesis of Allyldiisopropylbromosilane via Pd-catalyzed Bromination of Allyldiisopropylsilane Crude allyldiisopropylsilane (1.2 g), which was prepared as described in "Preparation of Allyldiisopropylsilane", was taken up in allyl bromide (15 mL) and purged for 15 minutes with $N_2$. $PdCl_2$ (16 mg, 1 mol % assuming silane purity of 100%) was added and the reaction was heated to 60° C. for 3 hours. Solvent (allyl bromide is both solvent and reagent) was removed by rotary evaporation, then the crude suspension was taken up in pentane (20 mL) and filtered. Removal of pentane by rotary evaporation yielded a pale brown liquid. Analysis by GC-MS Analysis Method 1 indicated a single product with a M/Z of 234/236 corresponding to molecular ions of allyldiisopropylbromosilane at a retention time of 6.5 min. NMR spectral data confirmed the assignment. $^1$H-NMR (400 MHz/$CHCl_3$) δ=5.8 (m, 1H), 5.0 (m, 2H), 1.9 (m, 2H), 1.0 (m, 14H).

Comparitive Example C-1

Attempted Synthesis of Allyldiisopropylbromosilane via N-Bromosuccinimide (NBS) Bromination of Allyldiisopropylsilane Crude allyldiisopropylsilane (1.2 g), which was prepared as described in "Preparation of Allyldiisopropylsilane", was taken up in dichloromethane (15 mL), cooled in an ice bath, and treated with 1.2 equivalents (assuming silane purity of 100%) of N-bromosuccinimide (1.6 g, 9.1 mmol) scoopwise over 15 minutes. Stirring was continued for 1 hour, maintaining the temperature, then a small aliquot was removed from the reaction mixture, and analyzed by GC-MS Analysis Method 1. The GC-MS analysis indicated two main peaks at retention times of 4.4 and 8.8, and smaller peaks at 5.8, 6.5, 8.6 and 9.9 minutes. Each of the peaks at 4.4 and 8.8 contributed about 40-45% of the total integrated area. The peak at 4.4 appears to correspond to the starting material, allyldiisopropylsilane (M/Z 156). The peak at 8.8 has a mass of M/Z 314 with a characteristic multiple bromine isotope pattern, corresponding to the dibrominated species, (2-bromopropyl)diisopropylbromosilane, which would be indicative of both the desired conversion of the hydrosilane to bromosilane and the undesired addition of bromine (hydrogen bromide) to the allyl group. Another half equivalent of N-bromosuccinimide was added to the reaction mixture, and the reaction continued.

After, another small aliquot was removed, GC-MS analysis (by GC-MS Analysis Method 1) indicated that the peak at 8.8 retention time made up 73% (by integration) of the total. NMR spectral data of the reaction products did not show the characteristic allyl multiplets that occur at 5.0 and 5.8 ppm.

Example 2

Synthesis of (Isopropenyldiisopropylsilyl)acetylene

Synthesis of Isopropenyldiisopropylbromosilane
(Also Referred to as
(Isopropenyldiisopropylsilyl)bromide Crude isopropenyldiisopropylsilane (7.8 g), which was prepared as described in "Preparation of Isopropenyldiisopropylsilane-Method 1", was dissolved in dry benzene (20 mL) in a round bottom flask that was then flushed with $N_2$ for several minutes. Allyl bromide (7.26 g, 60 mmol, 1.2 eq.) and $PdCl_2$ (50 mg, 0.25 mmol, 0.5 mol %) were added and the reaction mixture was heated to 60° C. overnight (15 hours). After cooling, solvent and excess allyl bromide was removed on a rotary evaporator, then the product was taken up in pentane (50 mL) and filtered through quantitative filter paper, which was rinsed with additional pentane (100 mL). Solvent was removed to yield 10.6 g of crude product as a light brown liquid.

Synthesis of (Isopropenyldiisopropylsilyl)acetylene

The crude isopropenyldiisopropylbromosilane (10.6 g) was treated with 75 mmol of lithium acetylide. The lithium acetylide was formed by saturating an anhydrous THF solution (at −78° C., 200 mL) with acetylene gas that had been passed through a −78° C. cold trap to remove acetone. No further drying of the acetylene gas was undertaken. Once the solution was presumed to be saturated (after 1 hour of flushing the gas through), the solution was treated with n-butyl-lithium (30 mL, 2.5 M in hexanes, 75 mmol) in a careful dropwise manner so as to maintain the temperature very close to −78° C. After this addition was completed, the isopropenyldiisopropylbromosilane was added as a concentrated solution (~5 M) in anhydrous THF dropwise to the reaction mixture. The temperature was maintained for an additional 1 hour, then allowed to gradually warm to room temperature. The reaction was quenched by the slow addition of a small amount of saturated ammonium chloride (about 5 mL) and additional water (50 mL). Pentane (100 mL) was added, and the organic layer was separated. The aqueous layer was extracted a second time with pentane (50 mL), and the organic layer separated. The organic layers were washed with water (3×50 mL), dried over $MgSO_4$, filtered, and concentrated on the rotary evaporator. No further purification was performed. Analysis of the liquid product was performed by GC-MS Analysis Method 2. This showed that the area under the peak corresponding to the desired product, (isopropenyldiisopropylsilyl)acetylene with a molecular weight of 180, was 87.34% of the total integrated area indicating a high purity.

Comparative Example C-2

Synthesis of (Isopropenyldiisopropylsilyl)acetylene

Synthesis of Isopropenyldiisopropylbromosilane
(Also Referred to as
(Isopropenyldiisopropylsilyl)bromide Crude isopropenyldiisopropylsilane (7.36 g), which was prepared as described in "Preparation of Isopropenyldiisopropylsilane-Method 1", was dissolved in dichloromethane (100 mL) and treated at 0° C. with N-bromosuccinimide (10.1 g, 56.6 mmol, 1.2 eq. assuming silane purity of 100%) scoopwise over 1 hour, then allowed to stir an additional hour while maintaining the temperature at 0° C. The solution was immediately filtered, and the solid cake rinsed with pentane. The solvent was removed, and the solid was taken up in pentane (50 mL) and filtered through quantitative filter paper, which was rinsed with additional pentane (100 mL). This procedure was repeated one more time, then removal of solvent yielded 10.6 g of the crude product as a hazy brown liquid.

Synthesis of (Isopropenyldiisopropylsilyl)acetylene

The crude isopropenyldiisopropylbromosilane (10.6 g) was treated with 75 mmol of lithium acetylide and the liquid product isolated using the same procedure as described in Example 2. The product was analyzed by GC-MS Analysis Method 2. This showed that the area under the peak corresponding to the desired product, (isopropenyldiisopropylsilyl)acetylene with a molecular weight of 180, was 31.64% of the total area indicating a significantly lower purity than that obtained in Example 2.

Isopropenyldiisopropylsilane was not observed, and isopropenyldiisopropylbromosilane accounted for 0.165% of the total integrated area.

Example 3

Synthesis of (Isopropenyldiisopropylsilyl)acetylene

Synthesis of Isopropenyldiisopropylbromosilane (Also Referred to as (Isopropenyldiisopropylsilyl)bromide Crude isopropenyldiisopropylsilane (2.8 g), which was prepared as described in "Preparation of Isopropenyldiisopropylsilane—Method 2", was taken up in allyl bromide (20 mL), and purged with $N_2$ for 15 minutes. $PdCl_2$ (32 mg, 1 mol %) was added and the suspension was heated to 60° C. for 12 hours. The suspension was concentrated by rotary evaporation, then taken up in pentane (40 mL) and filtered through quantitative filter paper, that was then rinsed with additional pentane (40 mL). Removal of solvent yielded 3.85 g of crude isopropenyldiisopropylbromosilane as a pale brown liquid.

Synthesis of (Isopropenyldiisopropylsilyl)acetylene

The crude isopropenyldiisopropylbromosilane (3.61 g) was added to a solution of 23 mmol of lithium acetylide in anhydrous THF (200 mL). The acetylide was prepared from acetylene gas and n-butyllithium. The acetylene gas was circulated through a dry ice/acetone (−78° C.) cold trap for 15 minutes while a round bottom flask, charged with the anhydrous THF, was separately cooled to −78° C. Then, the acetylene gas was bubbled through the THF solution for 1 hour, in order to saturate the THF solution with dissolved acetylene. n-Butyllithium (9.2 mL, 2.5 M in hexanes, 23 mmol) was then added dropwise over 1.5 hours, followed by removal of the acetylene line and continued stirring for 20 minutes. Finally, the crude bromosilane (3.61 g) was dissolved in anhydrous THF (5 mL) and added dropwise to the reaction mixture. The temperature was maintained at −78° C. throughout the process, then allowed to warm to room temperature over 15 hours. The reaction was quenched by the addition of water and saturated ammonium chloride solution (10 mL), then extracted into hexanes. The organic layer was washed with water, dried over $MgSO_4$, filtered, and concentrated to yield 2.4 g of crude (isopropenyldiisopropylsilyl)acetylene as a pale brown liquid. The product was analyzed by GC-MS Analysis Method 2. This showed that the area under the peak corresponding to the desired product, (isopropenyldiisopropylsilyl)acetylene with a molecular weight of 180, was 87.47% of the total integrated area indicating a high purity.

Comparative Example C-3. Synthesis of (Isopropenyldiisopropylsilyl)acetylene

Synthesis Of Isopropenyldiisopropylbromosilane (Also Referred to as (Isopropenyldiisopropylsilyl)bromide Crude isopropenyldiisopropylsilane (10 g), which was prepared as described in "Preparation of Isopropenyldiisopropylsilane—Method 2" was taken up in dichloromethane (120 mL) and cooled in an ice bath. N-Bromosuccinimide (13.7 g, 77 mmol, 1.2 eq. assuming silane purity of 100%) was added scoopwise over 1 hour, followed by an additional hour of stirring while maintaining the temperature. The suspension was filtered and the solid rinsed with pentane (50 mL). Solvent was removed by rotary evaporation and the suspension again taken up in pentane (70 mL), and filtered through quantitative filter paper, that was then rinsed with additional pentane (50 mL). Removal of solvent by rotary evaporation yielded crude isopropenyldiisopropylbromosilane (15 g) as a hazy, pale brown liquid.

Synthesis of (Isopropenyldiisopropylsilyl)acetylene

The crude isopropenyldiisopropylbromosilane (14.4 g) was added to a solution of 92 mmol of lithium acetylide in anhydrous THF (240 mL). The acetylide was prepared from acetylene gas and n-butyllithium. The acetylene gas was circulated through a dry ice/acetone (−78° C.) cold trap for 15 minutes while a round bottom flask, charged with the anhydrous THF, was separately cooled to −78° C. Then, the acetylene gas was bubbled through the THF solution for 1 hour, in order to saturate the THF solution with dissolved acetylene. n-Butyllithium (37 mL, 2.5 M in hexanes, 92 mmol) was then added dropwise over 1.5 hours, followed by removal of the acetylene line and continued stirring for 20 minutes. Finally, the crude bromosilane (14.4 g) was dissolved in anhydrous THF (15 mL) and added dropwise to the reaction mixture. The temperature was maintained at −78° C. throughout the process, then allowed to warm to room temperature over 15 hours. The reaction was quenched by the addition of water and saturated ammonium chloride solution (10 mL), then extracted into hexanes. The organic layer was washed with water, dried over $MgSO_4$, filtered, and concentrated to yield 9.8 g of crude (isopropenyldiisopropylsilyl)acetylene as a brown liquid. The product was analyzed by GC-MS Analysis Method 2. This showed that the area under the peak corresponding to the desired product, (isopropenyldiisopropylsilyl)acetylene with a molecular weight of 180, was 77.05% of the total area indicating a lower purity than that obtained in Examples 2 and 3. Isopropenyldiisopropylsilane was not observed, and isopropenyldiisopropylbromosilane accounted for 0.063% of the total integrated area.

The following embodiments of the invention are provided.
1. A process for preparing a compound of the formula

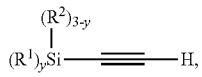

where $R^1$ and $R^2$ are (hetero)hydrocarbyl groups, and $R^1$ is not $R^2$, and y is 1 or 2,
comprising the steps of:
a) contacting a hydrocarbylsilane of the formula

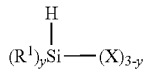

with an organometallic reagent of the formula $R^2\text{-}M^{m+}(X^1)_{m-1}$, wherein $M^{m+}$ an alkali- or alkali earth metal cation of valence m, where m is 1 or 2, $X^1$ is a halide, X is a halogen atom, and y is 1 or 2;
b) brominating the product of step a) with a transition metal bromination catalyst and an aliphatic bromo compound;
c) contacting the product of step b) with an organometallic compound of the formula

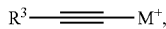

where M+ is an alkali- or alkali earth metal cation, $R^3$ is H— or an acetylene protecting group, and
where $R^3$ is an acetylene protecting group, removing the protecting group of the product of step c).
2. The process of embodiment 1, where each of $R^1$ and $R^2$ are selected from alkyl, alkenyl, cycloalkyl and aryl, or combinations thereof.
3. The process of embodiments 1 or 2 where $R^3$ is H—, and $R^3\text{-}\equiv\text{-}M^+$ is generated in situ by contacting acetylene with an alkyl lithium compound.
4. The process of any of the previous embodiments, where the transition metal bromination catalyst is a Group 10 transition metal halide and the aliphatic bromo compound is an alkyl- or allyl bromide.
5. The process of embodiment 4 wherein said transition metal halide is $PdCl_2$ or $NiCl_2$.
6. The process of any of the previous embodiments wherein the product of step
a) is of the formula:

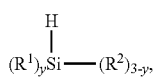

where
$R^1$ and $R^2$ are (hetero)hydrocarbyl groups, and $R^1$ is not $R^2$, and y is 1 or 2.
7. The process of any of the previous embodiments where the product of step b) is

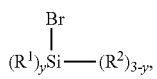

where
$R^1$ and $R^2$ are (hetero)hydrocarbyl groups, and $R^1$ is not $R^2$, and y is 1 or 2.

8. The process of any of the previous embodiments where the product of step c) is

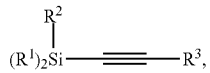

where
$R^1$ and $R^2$ are (hetero)hydrocarbyl groups, $R^3$ is H— or $(CH_3)_3$—Si—, and $R^1$ is not $R^2$.
9. The process of any of the previous embodiments, where $R^3$ is an acetylene protecting group, and step of removing the protecting group comprises contacting the product of step c) with alcoholic base or fluoride ion.
10. The process of any of the previous embodiments, where $R^3$ is $(CH_3)_3$—Si—.
11. The process of embodiment 10 where said step of removing the protecting group $R^3$ comprises treatment with alcoholic base.

What is claimed is:
1. A process for preparing a compound of the formula

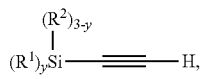

where $R^1$ and $R^2$ are (hetero)hydrocarbyl groups, and $R^1$ is not $R^2$, and y is 1 or 2,
comprising the steps of:
a) contacting a hydrocarbylsilane of the formula

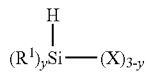

with an organometallic reagent of the formula $R^2\text{-}M^{m+}(X^1)_{m-1}$, wherein $M^{m+}$ an alkali- or alkali earth metal cation of valence m, where m is 1 or 2, $X^1$ is a halide, X is a halogen atom, and y is 1 or 2;
b) brominating the product of step a) with a transition metal bromination catalyst and an aliphatic bromo compound;
c) contacting the product of step b) with an organometallic compound of the formula

where M+ is an alkali- or alkali earth metal cation, $R^3$ is H- or an acetylene protecting group, and
where $R^3$ is an acetylene protecting group, removing the protecting group of the product of step c).
2. The process of claim 1, where each of $R^1$ and $R^2$ are selected from alkyl, alkyl, alkenyl, cycloalkyl and aryl, or combinations thereof.
3. The process of claim 1 where $R^3$ is H—, and $R^3\text{-}\equiv\text{-}M^+$ is generated in situ by contacting acetylene with an alkyl lithium compound.
4. The process of claim 1, where the transition metal bromination catalyst is a Group 10 transition metal halide and the aliphatic bromo compound is an alkyl- or allyl bromide.
5. The process of claim 4 wherein said transition metal halide is $PdCl_2$ or $NiCl_2$.

6. The process of claim 1 wherein the product of step a) is of the formula:

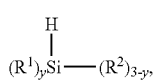

where
R$^1$ and R$^2$ are (hetero)hydrocarbyl groups, and R$^1$ is not R$^2$, and y is 1 or 2.

7. The process of claim 1 where the product of step b) is

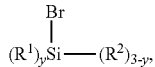

where
R$^1$ and R$^2$ are (hetero)hydrocarbyl groups, and R$^1$ is not R$^2$, and y is 1 or 2.

8. The process of claim 1 where the product of step c) is

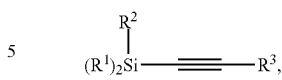

where
R$^1$ and R$^2$ are (hetero)hydrocarbyl groups, R$^3$ is H— or (CH$_3$)$_3$—Si—, and R$^1$ is not R$^2$.

9. The process of claim 1, where R$^3$ is an acetylene protecting group, and step of removing the protecting group comprises contacting the product of step c) with alcoholic base or fluoride ion.

10. The process of claim 1, where R$^3$ is (CH$_3$)$_3$—Si—.

11. The process of claim 10 where said step of removing the protecting group R$^3$ comprises treatment with alcoholic base.

* * * * *